US012709590B2

(12) United States Patent
Jain et al.

(10) Patent No.: US 12,709,590 B2
(45) Date of Patent: Aug. 18, 2026

(54) SYSTEM AND PROCESS FOR PRODUCING GLYCOLS

(71) Applicant: SABIC GLOBAL TECHNOLOGIES B.V., Bergen op Zoom (NL)

(72) Inventors: Jai Prakash Jain, Bangalore (IN); Uma Sankar, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 684 days.

(21) Appl. No.: 18/249,021

(22) PCT Filed: Oct. 14, 2021

(86) PCT No.: PCT/IB2021/059466
§ 371 (c)(1),
(2) Date: Apr. 13, 2023

(87) PCT Pub. No.: WO2022/079662
PCT Pub. Date: Apr. 21, 2022

(65) Prior Publication Data

US 2023/0406799 A1 Dec. 21, 2023

Related U.S. Application Data

(60) Provisional application No. 63/092,379, filed on Oct. 15, 2020.

(51) Int. Cl.
*C07C 29/10* (2006.01)
*C07C 41/03* (2006.01)

(52) U.S. Cl.
CPC ............ *C07C 29/106* (2013.01); *C07C 41/03* (2013.01)

(58) Field of Classification Search
CPC .................................................... C07C 29/106
See application file for complete search history.

(56) References Cited

U.S. PATENT DOCUMENTS 6,160,187 A * 12/2000 Strickler ............... C07C 29/106
568/867

FOREIGN PATENT DOCUMENTS

| | | | |
|---|---|---|---|
| CN | 1237953 | A | 12/1999 |
| CN | 1657514 | A | 8/2005 |
| CN | 1683292 | A | 10/2005 |
| CN | 102482182 | A | 5/2012 |

(Continued)

OTHER PUBLICATIONS

Elsinghort, R. "Optimization of the reactor section of a catalytic ethyleneglycol plant", Ch. 5, pp. 54-66, 1994.

(Continued)

*Primary Examiner* — Medhanit W Bahta
(74) *Attorney, Agent, or Firm* — Norton Rose Fulbright US LLP

(57) ABSTRACT

A system and a method for producing ethylene glycol are disclosed. Alkylene oxide and water are flowed into a first reactor unit and subjecting the alkylene oxide and water, in the first reactor unit, to first reaction conditions such that an effluent of the first reactor unit comprises an alkylene glycol, unreacted alkylene oxide, and unreacted water. At least a portion of the unreacted alkylene oxide may be routed to a second reaction unit and subjected to reaction conditions sufficient to produce additional alkylene glycol, wherein the second reactor unit is a reactive distillation column.

20 Claims, 4 Drawing Sheets

(56) References Cited

FOREIGN PATENT DOCUMENTS

| | | | |
|---|---|---|---|
| CN | 107021869 A | 8/2017 | |
| EP | 0929503 | 10/2001 | |
| EP | 3181542 | 6/2017 | |
| WO | WO-9814419 A1 * | 4/1998 | ........... C07C 29/106 |

OTHER PUBLICATIONS

Stichlmair J. et al., "Reactive Distillation Processes", *Chemical Engineering & Technology*, . Wiley, vol. 22, No., 2, pp. 95-103, 1999.

Zhu, F. et al., "Towards further internal heat integration in design of reactive distillation columns—Part IV: Application to a high-purity ethylene glycol reactive distillation column", *Chemical Engineering Science*, vol. 64, No. 15, pp. 3498-3509, 2009.

International Search Report and Written Opinion issued in corresponding International application PCT/IB2021/059466 mailed Feb. 3, 2022.

Kejin Huang et.al., "Towards further internal heat integration in design of reactive distillation columns"—Part III: Application to a MTBE reactive distillation column, Chemical Engineering Science, vol. 63, No. 1-20 pp. 2119-2134.

CN office action issued on Feb. 26, 2025 for the patent Application No. 202180070613.0 dated Apr. 14, 2023, 8 pages.

* cited by examiner

SYSTEM AND PROCESS FOR PRODUCING GLYCOLS

CROSS-REFERENCE TO RELATED APPLICATION

This application is a national phase under 35 U.S.C. § 371 of International Application No. PCT/IB2021/05946, filed Oct. 14, 2021, which claims the benefit of priority of U.S. Provisional Patent Application No. 63/092,379, filed Oct. 15, 2020, the entire contents of each of which are hereby incorporated by reference in their entirety.

FIELD OF INVENTION

The present invention generally relates to a system and a process for producing glycols. More specifically, the present invention relates to a system and a method for hydrating alkylene oxides to form glycols. Even more specifically, the present invention relates to a system and a method for controlling mono ethylene glycol to diethylene glycol ratio when these products are produced from ethylene oxide and water.

BACKGROUND OF THE INVENTION

Glycols are very useful compounds. For example, mono ethylene glycol (MEG) is used as an antifreeze and coolant for engines and intermediate for producing polyester fibers and polyethylene terephthalate (PET), which is used for producing plastic bottles. Diethylene glycol (DEG) can be used to produce polyurethanes, plasticizers, and organic solvents. Triethylene glycols (TEG) are often used as plasticizers and moisture-retaining agents. Polyethylene glycols (PEG) are used in perfumes, cosmetics, lubricants, and plasticizers.

Ethylene glycols can be produced via non-catalytic thermal hydration of ethylene oxide (EO) in a long plug flow reactor. The products from this method generally include mono ethylene glycol, diethylene glycol, triethylene glycol, and polyethylene glycol. Often, the market demand for each of these ethylene glycols varies with time. Thus, it would be desirable to control the production rate for each type of ethylene glycol during ethylene glycol production. However, it is highly challenging to manipulate the proportion of each of the ethylene glycol produced using this conventional method. Also, a higher proportion of mono ethylene glycols requires higher water in the reaction system, which will increase the energy consumption in the subsequent separation methods. Overall, while the methods of producing ethylene glycol exist, the need for improvements in this field persists in light of at least the aforementioned drawbacks with processes for producing ethylene glycols.

BRIEF SUMMARY OF THE INVENTION

A solution to at least some of the above-mentioned problems associated with the methods of producing ethylene glycols has been discovered. The solution resides in a process that produces ethylene glycols via thermal hydration of ethylene oxide in a system that includes at least two reactor units and a separation unit, in series. Embodiments of the invention, as described below, can help in providing a higher ratio of mono ethylene glycol to diethylene glycol. Additionally, embodiments of the invention can be configured to reduce energy consumption for producing ethylene glycols via reducing the high-water to-ethylene oxide ratio in the feed stream, which is required in convention ethylene glycol production systems.

In embodiments of the invention, a first reactor unit comprises a plug flow reactor and a second reactor unit comprises a reactive distillation column that also serves as the separation unit. In this way, the effluent from the plug flow reactor that is fed to the reactive distillation column undergoes complete, or almost complete, ethylene oxide conversion. The extent of conversion on ethylene oxide in first reactor is selected as optimum to achieve highest mono ethylene glycol to di-ethylene glycol ration in final product.

In embodiments of the invention, a first reactor unit comprises a plug flow reactor and a distillation column is adapted to receive effluent from the plug flow reactor, proceed the reaction, and separate the effluent of the plug flow reactor, and where a second reactor unit comprises a plug flow reactor adapted to react a bottoms stream from the distillation column. In this way, the effluent stream from the first reactor unit can be fed to the distillation column and be separated into a mono ethylene glycol-rich stream with a high water to ethylene oxide ratio and an ethylene oxide-rich stream with a low water to ethylene oxide ratio (i.e. lower water to ethylene oxide ratio than the mono ethylene glycol-rich stream). And the ethylene glycol-rich stream can be subsequently fed to the second reactor to produce additional mono ethylene glycol. This can be beneficial by increasing the mono ethylene glycol to diethylene glycol ratio in the product stream compared to the conventional methods. Additionally, in embodiments of the present invention, the ethylene oxide-rich stream, which is separated from the effluent stream of the first reactor, can be recycled back to the first reactor for producing additional ethylene glycol or can be sent for pure ethylene oxide production. Hence, embodiments of the present invention are capable of controllably increasing the mono ethylene to diethylene glycol ratio produced by thermal hydration of ethylene oxide, increasing the production efficiency, and reducing the production cost of ethylene glycol. Therefore, the method of the present invention provides a technical solution to at least some of the problems associated with the currently available methods for producing ethylene glycol.

Embodiments of the invention include a method of producing a glycol. The method includes flowing an alkylene oxide and water into a first reactor unit and subjecting the alkylene oxide and water, in the first reactor unit, to first reaction conditions such that an effluent of the first reactor unit comprises an alkylene glycol, unreacted alkylene oxide, and unreacted water. The method also includes flowing at least a portion of the unreacted alkylene oxide to a second reaction unit, for example, a reactive distillation unit, and subjecting the unreacted alkylene oxide in the second reactor unit to second reaction conditions sufficient to produce additional alkylene glycol. The extent of conversion on alkylene oxide in first reactor is selected as optimum to achieve highest mono alkylene glycol to di-alkylene glycol ratio in final product.

Embodiments of the invention include a method of producing ethylene glycol. The method includes flowing ethylene oxide and water into a first reactor unit and subjecting the ethylene oxide and water, in the first reactor unit, to first reaction conditions such that an effluent of the first reactor unit comprises mono ethylene glycol, unreacted ethylene oxide, and unreacted water. The method also includes flowing at least a portion of the unreacted ethylene oxide to a second reaction unit and subjecting the unreacted ethylene oxide in the second reactor unit to second reaction conditions sufficient to produce additional mono ethylene glycol.

Embodiments of the invention include a method of producing ethylene glycol. The method comprises flowing ethylene oxide and water into a first reactor. The method further comprises subjecting the ethylene oxide and water in the first reactor to reaction conditions such that an effluent of the first reactor comprises mono ethylene glycol, unreacted ethylene oxide, and unreacted water. Preferably, the extent of conversion on ethylene oxide in first reactor is selected as optimum to achieve highest mono ethylene glycol to diethylene glycol ratio in the final product. The method further comprises feeding the effluent of the first reactor to a reactive distillation column for complete conversion, or at least 98 wt. % conversion, of ethylene oxide to ethylene glycols. The method also involves using the reactive distillation column, according to embodiments of the invention, for separating the effluent of the first reactor into an overhead stream comprising unreacted water and unreacted ethylene oxide, which is fed back to the reactive distillation unit as a reflux, and a second stream comprising unreacted water and glycols. The second stream (bottom stream) can contain 11 to 25 wt. % mono ethylene glycol, 0.8 to 3 wt. % diethylene glycol, and 72 to 88 wt. % water.

Embodiments of the invention include a method of producing ethylene glycol. The method includes flowing ethylene oxide and water into a first reactor. The method includes subjecting the ethylene oxide and water in the first reactor under reaction conditions sufficient to produce mono ethylene glycol such that an effluent of the first reactor comprises unreacted water, unreacted ethylene oxide, and mono ethylene glycol. The method further comprises separating the effluent of the first reactor into a first stream comprising primarily unreacted water and unreacted ethylene oxide, collectively, and a second stream comprising primarily unreacted ethylene oxide, unreacted water, and mono ethylene glycol collectively. The method further still comprises flowing the second stream into a second reactor. The method further still comprises subjecting the second stream in the second reactor to reaction conditions sufficient to produce additional mono ethylene glycol and convert more than 98 wt. %, preferably more than 99.9 wt. %, of the ethylene oxide flowed into the second reactor.

Embodiments of the invention include a method of producing an alkylene glycol. The method comprises flowing an alkylene oxide and water into a first reactor. The method further comprises subjecting the alkylene oxide and water in the first reactor to reaction conditions such that an effluent of the first reactor comprises mono alkylene glycol, unreacted alkylene oxide, and unreacted water. Preferably, the extent of conversion on ethylene oxide in first reactor is selected as optimum to achieve highest mono ethylene glycol to diethylene glycol ratio in final product. The method further comprises feeding the effluent of the first reactor to a reactive distillation column for complete conversion, or at least 98 wt. %, of alkylene oxide to alkylene glycols. The method also involves using the reactive distillation column, according to embodiments of the invention, which is also used in separating the effluent of the first reactor into a first stream comprising primarily unreacted water and unreacted alkylene oxide, collectively, and a second stream comprising primarily unreacted alkylene oxide, unreacted water, and mono alkylene glycol, collectively.

Embodiments of the invention include a method of producing an alkylene glycol. The method includes flowing an alkylene oxide and water into a first reactor. The method includes subjecting the alkylene oxide and water in the first reactor under reaction conditions sufficient to produce mono alkylene glycol such that an effluent of the first reactor comprises unreacted water, unreacted alkylene oxide, mono alkylene glycol. The method further comprises separating the effluent of the first reactor into a first stream comprising primarily unreacted water and unreacted alkylene oxide, collectively, and a second stream comprising primarily unreacted alkylene oxide, unreacted water, and mono alkylene glycol collectively. The method further still comprises flowing the second stream into a second reactor. The method further still comprises subjecting the second stream in the second reactor to reaction conditions sufficient to produce additional mono alkylene glycol and convert more than 98 wt. %, preferably more than 99.9 wt. % of the alkylene oxide flowed into the second reactor.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, ethylene glycols including mono ethylene glycol, diethylene glycol, triethylene glycol and polyethylene glycols are produced by thermal hydration of ethylene oxide in a plug-flow type reactor. The conventional methods can improve the mono ethylene glycol/diethylene glycol ratio only by increasing the water to ethylene oxide ratio in the reactor, which will increase the energy required for separation in the downstream. The present invention provides a solution to at least this problem. The solution is premised on a method of producing ethylene glycol via thermal hydration of ethylene oxide in a system that comprises, for example, either one reactor and a reactive distillation column in series or at least two reactors and a distillation column in series. For a system with a reactor and a reactive distillation column, the effluent stream from the reactor undergoes further conversion in the reactive distillation column, which may operate in partial or total reflux, and is also separated in the reactive distillation column to produce (1) an overhead stream of unreacted ethylene oxide which is rich in ethylene oxide and (2) a bottoms stream, which is a mono ethylene glycol-rich stream. The overhead stream of ethylene oxide-rich stream is fed back to the reactive distillation column after condensation, according to embodiments of the invention. The ethylene oxide is substantially fully converted into ethylene glycols in the reactive distillation column, resulting in higher mono ethylene glycol to diethylene glycol ratio. For a system with two reactors and a distillation column, the effluent stream from the first reactor is separated into an ethylene oxide-rich stream with a low water to ethylene oxide ratio and a mono ethylene glycol-rich stream with a high water to ethylene oxide ratio. The mono ethylene glycol-rich stream is fed into the second reactor for fully converting the ethylene oxide to glycols. The ethylene oxide-rich stream can be recycled back to the first reactor. Therefore, the production ratio of mono ethylene glycol to diethylene glycol in the product stream is increased compared to the conventional methods. These and other non-limiting aspects of the present invention are discussed in further detail in the following sections.

A. System for Producing Ethylene Glycol

Figure 1:
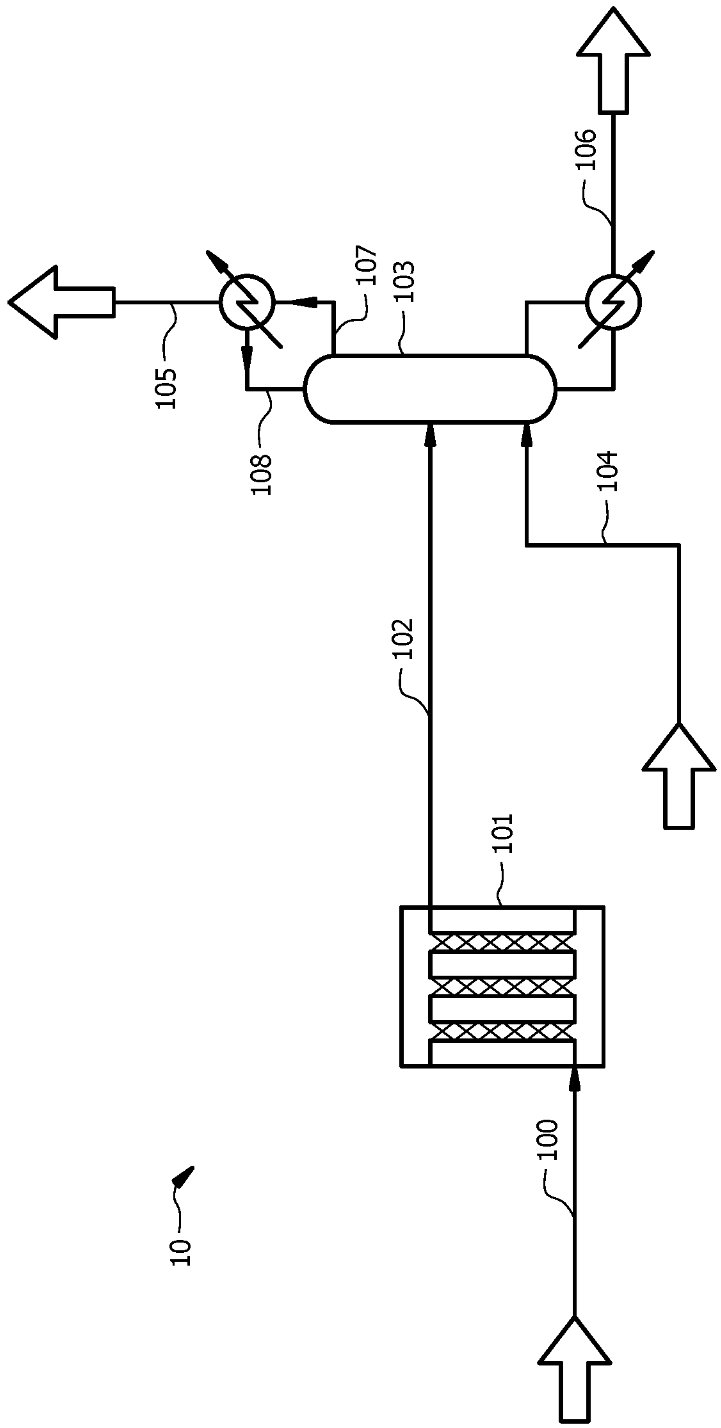
FIG. 1 shows a schematic diagram of a system for producing ethylene glycol, according to embodiments of the invention.

In embodiments of the invention, a system for producing ethylene glycol can include a first reactor unit and a second reactor unit that also performs a separation function. According to embodiments of the invention, the first reactor unit can be a reactor such as a plug flow reactor and the second reactor unit can be a reactive distillation column for continued thermal hydration of ethylene oxide in the effluent stream of the first reactor unit, where the reactive distillation column also separates the effluent stream of the first reactor unit. With reference to FIG. 1, a schematic diagram is shown of system 10 for producing ethylene glycol.

According to embodiments of the invention, system 10 comprises reactor 101 configured to receive feed stream 100 comprising primarily water and ethylene oxide. In embodiments of the invention, reactor 101 comprises a plug flow type reactor. Reactor 101 may be configured to subject water and ethylene oxide to reaction conditions sufficient to produce ethylene glycol(s). The ethylene glycol(s) may include mono ethylene glycol, diethylene glycol, triethylene glycol, polyethylene glycol, or any combination thereof. In embodiments of the invention, reactor 101 contains substantially no catalyst or no catalyst. Thus, the reaction conditions may be non-catalytic reaction conditions. Reactor 101 may be further configured to release effluent stream 102 therefrom. Effluent stream 102 may comprise unreacted water, unreacted ethylene oxide, mono ethylene glycol, diethylene glycol, triethylene glycol, polyethylene glycol, or any combination thereof. The extent of conversion of ethylene oxide in first reactor is selected as optimum to achieve highest mono ethylene glycol to di-ethylene glycol ratio in the final product.

According to embodiments of the invention, reactor 101 has a reaction residence time of 0.5 to 8 minutes and all ranges and values there between including ranges of 0.5 to 1.0 minutes, 1.0 to 1.5 minutes, 1.5 to 2.0 minutes, 2.0 to 2.5 minutes, 2.5 to 3.0 minutes, 3.0 to 3.5 minutes, 3.5 to 4.0 minutes, 4.0 to 4.5 minutes, 4.5 to 5.0 minutes, 5.0 to minutes, 5.5 to 6.0 minutes, 6.0 to 6.5 minutes, 6.5 to 7.0 minutes, 7.0 to 7.5 minutes, and 7.5 to 8.0 minutes. Also, the residence time for reactor 101 may be set to achieve a maximum MEG to DEG ratio of the system. Reactor 101 may comprise a heating mechanism adapted to heat water and ethylene oxide to a reaction temperature sufficient to produce ethylene glycol. The heating mechanism may include a heat exchanger located upstream to an inlet of reactor 101.

In embodiments of the invention, an outlet of reactor 101 is in fluid communication with an inlet of reactive distillation column 103 such that effluent stream 102 flows from reactor 101 to reactive distillation column 103. According to embodiments of the invention, reactive distillation column 103 is adapted to separate effluent stream 102 into a plurality of streams including overhead stream 107, part of which is fed back to the column as reflux 108, and part of which is some non-condensable gases, if any (stream 105), and bottoms stream 106. Further, in embodiments of the invention, reactive distillation column 103 is adapted to provide reaction conditions so that unreacted ethylene oxide is converted to ethylene glycol. For example, reactive distillation column 103 may have an inlet for receiving water stream 104 to react with the ethylene oxide in reactive distillation column 103. Further, reactive distillation column 103 may be operated to provide reaction conditions therein such that unreacted ethylene oxide in effluent stream 102 is converted to ethylene glycol. Overhead stream 107 may comprise primarily unreacted water, and unreacted ethylene oxide, collectively. Bottoms stream 106 may comprise primarily unreacted water, mono ethylene glycol, collectively, which is fed back to the column, in embodiments of the invention. Non-condensable gases (if any) can be separated as stream 105. Bottoms stream 106 may further comprise diethylene glycol, triethylene glycol, polyethylene glycol, or combinations thereof.

Figure 2:
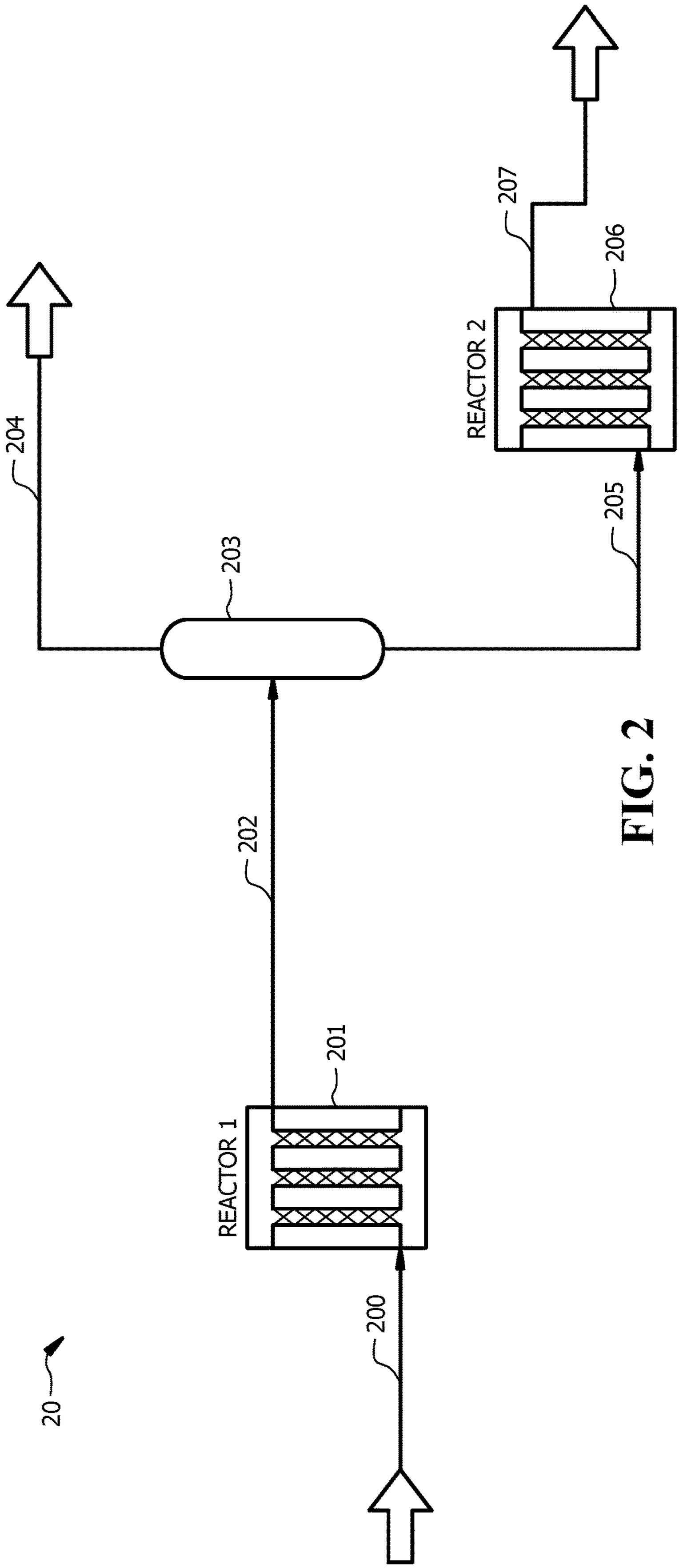
FIG. 2 shows a schematic diagram of a system for producing ethylene glycol, according to embodiments of the invention.

In embodiments of the invention, the system for producing ethylene glycol can include two reactors in series for thermal hydration of ethylene oxide, and a separation unit for separating the effluent stream from the first reactor. With reference to FIG. 2, a schematic diagram is shown of system 20 for producing ethylene glycol.

According to embodiments of the invention, system 20 comprises first reactor 201 configured to receive feed stream 200 comprising primarily water and ethylene oxide. As an alternative to or in addition to feed stream 200, water and ethylene oxide can be fed to first reactor 201 separately. In embodiments of the invention, first reactor 201 includes a plug flow type of reactor. First reactor 201 may be further configured to subject water and ethylene oxide to reaction conditions sufficient to produce ethylene glycol(s). The ethylene glycol(s) may include mono ethylene glycol, diethylene glycol, triethylene glycol, polyethylene glycol, or combinations thereof. In embodiments of the invention, first reactor 201 contains substantially no catalyst or no catalyst. Thus, the reaction conditions may be non-catalytic reaction conditions. First reactor 201 may be further configured to release first effluent stream 202 therefrom. First effluent stream 202 may comprise unreacted water, unreacted ethylene oxide, mono ethylene glycol, diethylene glycol, triethylene glycol, polyethylene glycol, or combinations thereof.

According to embodiments of the invention, first reactor 201 has a reaction residence time of 0.5 to 8.0 minutes and all ranges and values there between including ranges of 0.5 to 1.0 minutes, 1.0 to 1.5 minutes, 1.5 to 2.0 minutes, 2.0 to 2.5 minutes, 2.5 to 3.0 minutes, 3.0 to 3.5 minutes, 3.5 to 4.0 minutes, 4.0 to 4.5 minutes, 4.5 to 5.0 minutes, 5.0 to 5.5 minutes, 5.5 to 6.0 minutes, 6.0 to 6.5 minutes, 6.5 to 7.0 minutes, 7.0 to 7.5 minutes, and 7.5 to 8.0 minutes. First reactor 201 may comprise a heating mechanism adapted to heat water and ethylene oxide to a reaction temperature sufficient to produce ethylene glycol. The heating mechanism may include a heat exchanger located upstream to an inlet of first reactor 201.

In embodiments of the invention, an outlet of first reactor 201 is in fluid communication with an inlet of separation unit 203 such that first effluent stream 202 flows from first reactor 201 to separation unit 203. According to embodiments of the invention, separation unit 203 is adapted to separate first effluent stream 202 into a plurality of streams including first stream 204 and second stream 205. First stream 204 may comprise primarily unreacted water, and unreacted ethylene oxide, collectively. Second stream 205 may comprise unreacted water, unreacted ethylene oxide, and mono ethylene glycol, collectively. Second stream 205 may further comprise diethylene glycol, triethylene glycol, polyethylene glycol, or combinations thereof. In embodiments of the invention, separation unit 203 includes a distillation unit, flash vessel, or combinations thereof.

According to embodiments of the invention, a first outlet of separation unit 203 may be in fluid communication with second reactor 206 such that second stream 205 flows from separation unit 203 to second reactor 206. In embodiments of the invention, second reactor 206 is adapted to subject second stream 205 to reaction conditions sufficient to produce additional ethylene glycol and form product stream 207 that flows from second reactor 206. In embodiments of the invention, second reactor 206 may be a plug flow type reactor. In embodiments of the invention, second reactor 206 has a reaction residence time that results in complete conversion of ethylene oxide. According to embodiments of the invention, second reactor 206 can be substantially the same as first reactor 201.

According to embodiments of the invention, a second outlet of separation unit 203 may be in fluid communication with an inlet of first reactor 201 such that first stream 204 flows from separation unit 203 to first reactor 201. First reactor 201 may be further adapted to react unreacted ethylene oxide and unreacted water of first stream 204 to form additional ethylene glycol.

B. Method of Producing Ethylene Glycol

Figure 3:
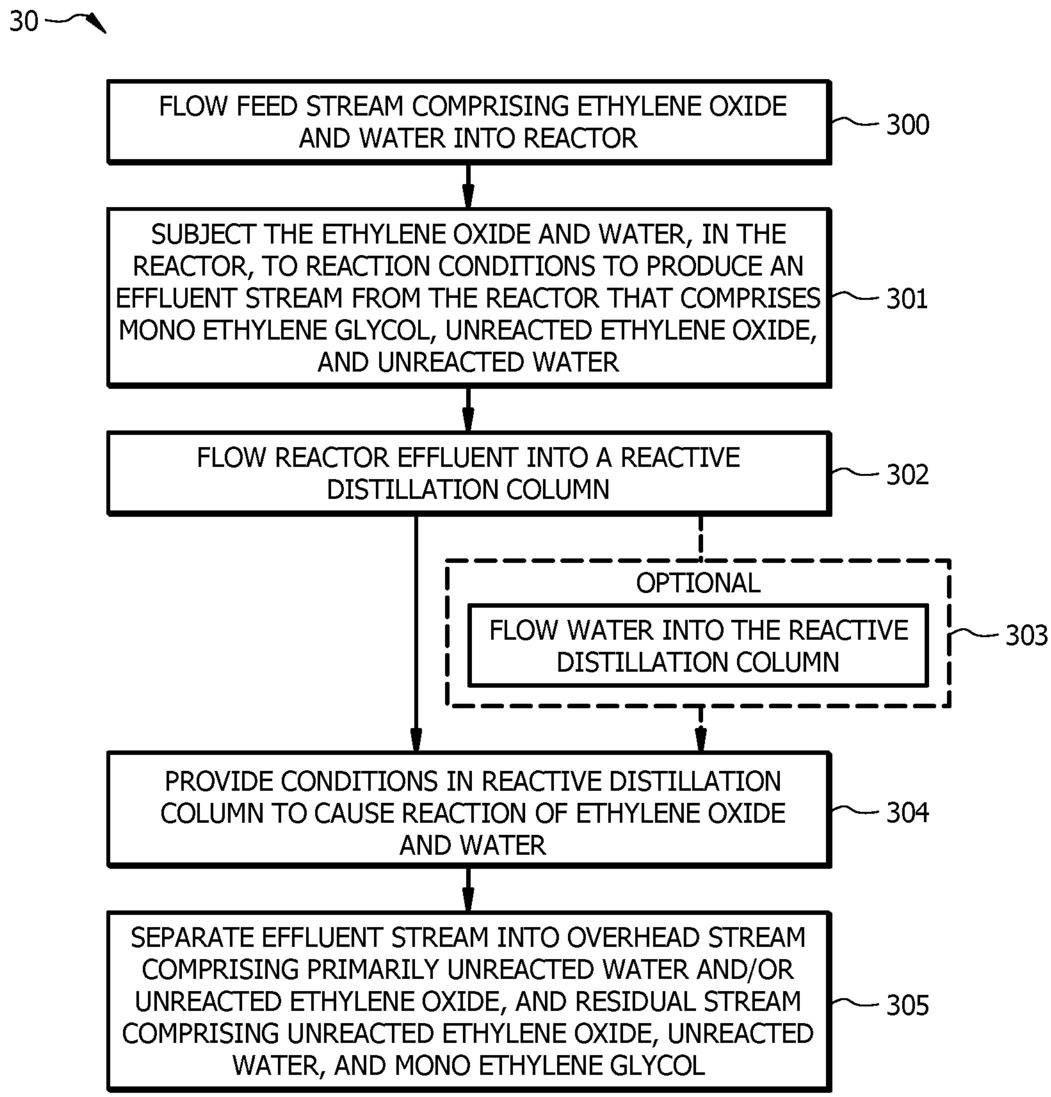
FIG. 3 shows a schematic flowchart of a method of producing ethylene glycol, according to embodiments of the invention.

A method of producing ethylene glycol via thermal hydration of ethylene oxide has been discovered. The method may be capable of increasing the ratio of mono ethylene glycol to diethylene glycol in the product stream compared to conventional methods. As shown in FIG. 3, embodiments of the invention include method 30 for producing ethylene glycol. Method 30 may be implemented by system 10, as shown in FIG. 1. According to embodiments of the invention, method 30 includes flowing feed stream 100 comprising ethylene oxide and water into reactor 101, as shown in block 300. In embodiments of the invention, feed stream 100 includes a water-to-ethylene oxide ratio of 10 to 25 (by mole) and all ranges and values there between including ranges of 10 to 11, 11 to 12, 12 to 13, 13 to 14, 14 to 15, 15 to 16, 16 to 17, 17 to 18, 18 to 19, 19 to 20, 20 to 21, 21 to 22, 22 to 23, 23 to 24, and 24 to 25, by mole. In embodiments of the invention, feed stream 100 may be at an inlet temperature of 120 to 160° C. before it flows into reactor 101 and all ranges and values there between including ranges of 120 to 121° C., 121 to 122° C., 122 to 123° C., 123 to 124° C., 124 to 125° C., 125 to 126° C., 126 to 127° C., 127 to 128° C., 128 to 129° C., 129 to 130° C., 130 to 131° C., 131 to 132° C., 132 to 133° C., 133 to 134° C., 134 to 135° C., 135 to 136° C., 136 to 137° C., 137 to 138° C., 138 to 139° C., 139 to 140° C., 140 to 141° C., 141 to 142° C., 142 to 143° C., 143 to 144° C., 144 to 145° C., 145 to 146° C., 146 to 147° C., 147 to 148° C., 148 to 149° C., 149 to 150° C., 150 to 151° C., 151 to 152° C., 152 to 153° C., 153 to 154° C., 154 to 155° C., 155 to 156° C., 156 to 157° C., 157 to 158° C., 158 to 159° C., and 159 to 160° C. As an alternative or in addition to feed stream 100, ethylene oxide and water may be separately flowed into reactor 101.

In embodiments of the invention, as shown in block 301, method 30 includes subjecting the ethylene oxide and water in reactor 101 to reaction conditions to cause a reaction of ethylene oxide and water such that effluent stream 102 of reactor 101 comprises mono ethylene glycol, unreacted ethylene oxide, and unreacted water. According to embodiments of the invention, effluent stream 102 further comprises diethylene glycol, triethylene glycol, polyethylene glycol, or combinations thereof. In embodiments of the invention, reaction conditions at block 301 comprise a reactor inlet temperature in the range of 120 to 160 and all ranges and values there between including ranges of 120 to 122° C., 122 to 124° C., 124 to 126° C., 126 to 128° C., 128 to 130° C., 130 to 132° C., 132 to 134° C., 134 to 136° C., 136 to 138° C., 138 to 140° C., 140 to 142° C., 142 to 144° C., 144 to 146° C., 146 to 148° C., 148 to 150° C., 150 to 152° C., 152 to 154° C., 154 to 156° C., 156 to 158° C., and 158 to 160° C. Reaction conditions at block 301 may include a reaction pressure of 18 to 25 bar and all ranges and values there between including 19 bar, 20 bar, 21 bar, 22 bar, 23 bar, and 24 bar. Reaction conditions at block 301 may include residence time of reactor 101 in a range of 0.5 to 8.0 minutes and all ranges and values there between including ranges of 0.5 to 1.0 minutes, 1.0 to 1.5 minutes, 1.5 to 2.0 minutes, 2.0 to 2.5 minutes, 2.5 to 3.0 minutes, 3.0 to 3.5 minutes, 3.5 to 4.0 minutes, 4.0 to 4.5 minutes, 4.5 to 5.0 minutes, 5.0 to 5.5 minutes, 5.5 to 6.0 minutes, 6.0 to 6.5 minutes, 6.5 to 7.0 minutes, 7.0 to 7.5 minutes, and 7.5 to 8.0 minutes. In embodiments of the invention, reactor 101 is operated with substantially no catalyst or no catalyst.

According to embodiments of the invention, effluent stream 102 includes 8 to wt. % mono ethylene glycol, 1 to 8 wt. % ethylene oxide, and 75 to 89 wt. % water. In embodiments of the invention, effluent stream 102 may further include 0.5 to 2 wt. % diethylene glycol.

In embodiments of the invention, as shown at block 302, method 30 further includes flowing effluent stream 102 to reactive distillation column 103. Embodiments of the invention can include flowing water stream 104 into reactive distillation column 103, as shown at block 303 (optional). And block 304 involves, according to embodiments of the invention, providing reaction conditions in reactive distillation column 103 such that unreacted ethylene oxide in effluent stream 102 is reacted with water from water stream 104 and/or unreacted water in the effluent stream to achieve complete or almost complete (e.g., 98 wt. %) conversion of ethylene oxide to ethylene glycol, in reactive distillation column 103. According to embodiments of the invention, water stream 104 enters reactive distillation column 103 at a temperature in a range of 125 to 150° C. and all ranges and values there between including ranges of 125 to 126° C., 126 to 127° C., 127 to 128° C., 128 to 129° C., 129 to 130° C., 130 to 131° C., 131 to 132° C., 132 to 133° C., 133 to 134° C., 134 to 135° C., 135 to 136° C., 136 to 137° C., 137 to 138° C., 138 to 139° C., 139 to 140° C., 140 to 141° C., 141 to 142° C., 142 to 143° C., 143 to 144° C., 144 to 145° C., 145 to 146° C., 146 to 147° C., 147 to 148° C., 148 to 149° C., and 149 to 150° C., and a pressure range of 15 to 25 bar and all ranges and values there between including ranges of 16 bar, 17 bar, 18 bar, 19 bar, 20 bar, 21 bar, 22 bar, 23 bar, and 24 bar. In embodiments of the invention, reactive distillation column 103, at block 305, also involves concurrently separating effluent stream 102 into overhead stream 105 comprising primarily unreacted water and unreacted ethylene oxide, collectively, and bottoms stream 106 comprising primarily unreacted water, and mono ethylene glycol, collectively. In embodiments of the invention, overhead stream 107 and 108 comprise 1 to 16 wt. % unreacted ethylene oxide and 83 to 99 wt. % unreacted water. Bottoms steam 106 may comprise 72 to 88 wt. % unreacted water, 0 to 0.1 wt. % unreacted oxide, and 11 to 25 wt. % mono ethylene glycol. It should be noted that in embodiments of the invention, complete conversion of ethylene oxide is expected which would result in 0 wt. % ethylene oxide in bottoms stream 106. In embodiments of the invention, bottoms stream 106 may further include diethylene glycol, triethylene glycol, polyethylene glycol, or combinations thereof.

Figure 4:
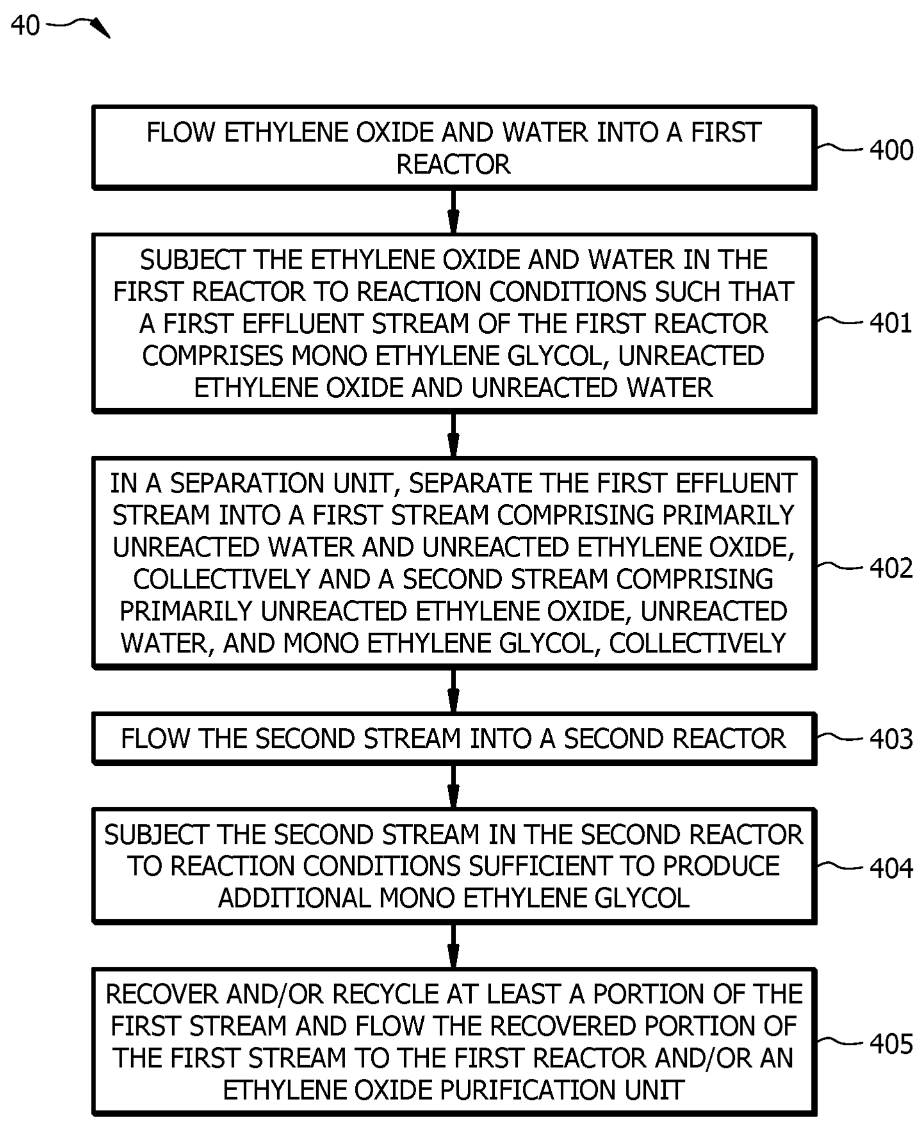
FIG. 4 shows a schematic flowchart of a method of producing ethylene glycol, according to embodiments of the invention.

A method of producing ethylene glycol via thermal hydration of ethylene oxide has been discovered. The method may be capable of increasing the ratio of mono ethylene glycol to diethylene glycol in the product stream compared to conventional methods. The method may further increase the conversion rate of ethylene oxide. As shown in FIG. 4, embodiments of the invention include method 40 for producing ethylene glycol. Method 40 may be implemented by system 20, as shown in FIG. 2. According to embodiments of the invention, as shown in block 400, method 40 includes flowing feed stream 200 comprising ethylene oxide and water into first reactor 201. In embodiments of the invention, feed stream 200 includes a water-to-ethylene oxide ratio of 10 to 25 (by mole) and all ranges and values there between including 10 to 11, 11 to 12, 12 to 13, 13 to 14, 14 to 15, 15 to 16, 16 to 17, 17 to 18, 18 to 19, 19 to 20, 20 to 21, 21 to 22, 22 to 23, 23 to 24, and 24 to 25, by mole. In embodiments of the invention, feed stream 200 may be at a temperature of 120 to 160° C. before it flows into first reactor 201 and all ranges and values there between including ranges of 120 to 121° C., 121 to 122° C., 122 to 123° C., 123 to 124° C., 124 to 125° C., 125 to 126° C., 126 to 127° C., 127 to 128° C., 128 to 129° C., 129 to 130° C., 130 to 131° C., 131 to 132° C., 132 to 133° C., 133 to 134° C., 134 to 135° C., 135 to 136° C., 136 to 137° C., 137 to 138° C., 138 to 139° C., 139 to 140° C., 140 to 141° C., 141 to 142° C., 142 to 143° C., 143 to 144° C., 144 to 145° C., 145 to 146° C., 146 to 147° C., 147 to 148° C., 148 to 149° C., 149 to 150° C., 150 to 151° C., 151 to 152° C., 152 to 153° C., 153 to 154° C., and 154 to 155° C., 155 to 156° C., 156 to 157° C., 157 to 158° C., 158 to 159° C., and 159 to 160° C. As an alternative or in addition to feed stream 200, ethylene oxide and water may be separately flowed into first reactor 201.

In embodiments of the invention, as shown in block 401, method 40 includes subjecting the ethylene oxide and water in first reactor 201 to reaction conditions to cause a reaction between ethylene oxide and water such that first effluent stream 202 of first reactor 201 comprises mono ethylene glycol, unreacted ethylene oxide, and unreacted water. According to embodiments of the invention, first effluent stream 202 further comprises diethylene glycol, triethylene glycol, polyethylene glycol, or combinations thereof. In embodiments of the invention, reactor inlet conditions at block 401 comprise a reaction temperature in the range of 120 to 160° C. and all ranges and values there between including ranges of 120 to 121° C., 121 to 122° C., 122 to 123° C., 123 to 124° C., 124 to 125° C., 125 to 126° C., 126 to 127° C., 127 to 128° C., 128 to 129° C., 129 to 130° C., 130 to 131° C., 131 to 132° C., 132 to 133° C., 133 to 134° C., 134 to 135° C., 135 to 136° C., 136 to 137° C., 137 to 138° C., 138 to 139° C., 139 to 140° C., 140 to 141° C., 141 to 142° C., 142 to 143° C., 143 to 144° C., 144 to 145° C., 145 to 146° C., 146 to 147° C., 147 to 148° C., 148 to 149° C., 149 to 150° C., 150 to 151° C., 151 to 152° C., 152 to 153° C., 153 to 154° C., 154 to 155° C., 155 to 156° C., 156 to 157° C., 157 to 158° C., 158 to 159° C. and 159 to 160° C. Reaction conditions at block 401 may include a reactor inlet pressure of 18 to 25 bar and all ranges and values there between including 19 bar, 20 bar, 21 bar, 22 bar, 23 bar, and 24 bar. Reaction conditions at block 401 may include a residence time of first reactor 201 in a range of 0.5 to 8.0 minutes and all ranges and values there between including ranges of 0.1 to 0.5 minutes, 0.5 to 1.0 minutes, 1.0 to 1.5 minutes, 1.5 to 2.0 minutes, 2.0 to 2.5 minutes, 2.5 to 3.0 minutes, 3.0 to 3.5 minutes, and 3.5 to 4.0 minutes, 4.0 to 4.5 minutes, 4.5 to 5.0 minutes, 5.0 to 5.5 minutes, 5.5 to 6.0 minutes, 6.0 to 6.5 minutes, 6.5 to 7.0 minutes, 7.0 to 7.5 minutes, and 7.5 to 8.0 minutes. In embodiments of the invention, first reactor 201 is operated with substantially no catalyst or no catalyst.

According to embodiments of the invention, separating of first effluent stream 202 to produce first stream 204 and second stream 205 at block 402 is performed at an overhead boiling temperature range of 150 to 180° C. and a pressure range of 6 to 20 bar. In embodiments of the invention, first stream 204 comprises 69 to 93% water, 0.6 to 1.3% mono ethylene glycol, and 6 to 29% ethylene oxide, and second stream 205 comprises 77 to 87% water, 11-20% mono ethylene glycol, 0.8 to 2.6% diethylene glycol, 0.04 to 0.4% triethylene glycol, and 0.0006 to 0.02% ethylene oxide.

According to embodiments of the invention, as shown in block 403, method further includes flowing second stream 205 into second reactor 206. In embodiments of the invention, as shown in block 404, method 40 includes subjecting second stream 205 in second reactor 206 to reaction conditions sufficient to produce additional mono ethylene glycol and convert more than 98 wt. % of the ethylene oxide flowed into second reactor 206. At block 404, product stream 207 from second reactor 206 may include 11 to 25 wt. % mono ethylene glycol, and 0.8 to 3.0 wt. % diethylene glycol. In embodiments of the invention, at block 404, all ethylene oxide flowed into second reactor 206 is converted.

In embodiments of the invention, reaction conditions at block 404 include a reactor inlet temperature in a range of 160 to 220° C. and all ranges and values there between including ranges of 160 to 162° C., 162 to 164° C., 164 to 166° C., 166 to 168° C., 168 to 170° C., 170 to 172° C., 172 to 174° C., 174 to 176° C., 176 to 178° C., 178 to 180° C., 180 to 182° C., 182 to 184° C., 184 to 186° C., 186 to 188° C., 188 to 190° C., 190 to 192° C., 192 to 194° C., 194 to 196° C., 196 to 198° C., 198 to 200° C., 200 to 202° C., 202 to 204° C., 204 to 206° C., 206 to 208° C., 208 to 210° C., 210 to 212° C., 212 to 214° C., 214 to 216° C., 216 to 218° C., and 218 to 220° C. Reaction conditions at block 404 may include a reaction pressure of 10 to 20 bar and all ranges and values there between including 10 to 11 bar, 11 to 12 bar, 12 to 13 bar, 13 to 14 bar, 14 to 15 bar, 15 to 16 bar, 16 to 17 bar, 17 to 18 bar, 18 to 19 bar, and 19 to 20 bar.

In embodiments of the invention, the reaction conditions at block 404 include a residence time of second reactor 206 for complete conversion of ethylene oxide. In embodiments of the invention, second reactor 206 is operated without catalyst or substantially without catalyst therein. According to embodiments of the invention, as shown in block 405, method 40 further includes recovering and/or recycling at least a portion, preferably all, of first stream 204 and flowing the recovered and/or recycled portion of first stream 204 to first reactor 201. As an alternative to or in addition to flowing the recovered and/or recycled portion of first stream 204 to first reactor 201, the recovered and/or recycled portion of first stream 204 can be flowed to an ethylene oxide purification unit for ethylene oxide production.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLES

Simulations on Ethylene Glycol Production

Simulations of ethylene glycol production using the system of the present invention were run in Aspen PLUS™ platform. Feed to the first reactor contains only ethylene oxide (EO) and water.

Case A: Comparison of normal operation of a convention 1 system (a single plug flow reactor (PFR)) with operation of a system that includes a plug flow reactor and a reactive distillation column in series as shown in FIG. 1.

Example 1: Single Plug Flow Reactor+Reactive Distillation Column without Supplemental Water to the Reactive Distillation Column, Water to EO Ratio: 22:1 (by Molar) in Feed Stream to Plug Flow Reactor Example 1 was simulated for a reactant composition of 22:1 water to ethylene oxide ratio by molar in a plug flow reactor. After an optimum conversion, the reaction mixture was fed to a reactive distillation column where complete reaction was achieved. The simulated reaction conditions and results for Example 1 are shown in Table 1.

TABLE 1

| | FEED (100) | PFROUT (102) | WATER (104) | FINAL (106) |
|---|---|---|---|---|
| Temperature, ° C. | 145 | 183.89 | 130 | 202.65 |
| Pressure, bar | 20 | 20 | 20 | 15.7 |
| Flow, Kg/hr | | | | |
| EO | 43654.95 | 9814.16 | | 0 |
| Water | 392895 | 379628.13 | 0 | 375802.78 |
| MEG | 0 | 43791.8 | | 56331.11 |
| DEG | 0 | 3184.45 | | 4233.97 |
| TEG | 0 | 131.41 | | 180.25 |
| EO conversion in PFR | | 77.52% | | |
| Final MEG/DEG ratio (by weight) | | 13.31 | | |

Example 2: Single Plug Flow Reactor+Reactive Distillation Column with Supplemental Water to the Reactive Distillation Column; Overall Water to Ethylene Oxide Ratio: 22:1 (by Molar)

In Example 2, the simulation involved a reactant composition containing 12:1 molar water to ethylene oxide was fed to a reactor and after an optimum conversion, the reaction mixture was fed to a reactive distillation column wherein water was fed from the top tray (resulting in an overall water used in the process corresponds to a water to ethylene oxide molar ratio of 22:1). The simulated reaction conditions and results for Example 2 are shown in Table 2. Comparison between Table 2 and Table 1 shows that the system is capable of reducing required water to ethylene oxide in initial feed stream to the plug flow reactor and achieving higher MEG/DEG ratio in the product stream.

TABLE 2

| | FEED (100) | PFROUT (102) | WATER (104) | FINAL (106) |
|---|---|---|---|---|
| Temperature, ° C. | 145 | 181.87 | 130 | 202.65 |
| Pressure, bar | 20 | 20 | 20 | 15.7 |
| Flow, Kg/hr | | | | |
| EO | 43654.95 | 24710.66 | | 0 |
| Water | 215140 | 207720.98 | 177755 | 375818.36 |
| MEG | 0 | 24462.5 | | 56229.63 |
| DEG | 0 | 1823.16 | | 4306.03 |
| TEG | 0 | 77.65 | | 194.08 |

TABLE 2-continued

| | FEED (100) | PFROUT (102) | WATER (104) | FINAL (106) |
|---|---|---|---|---|
| EO conversion in PFR | | 43.4% | | |
| Final MEG/DEG ratio (by weight) | | 13.6 | | |

It can be observed from Table 1 and Table 2 that Example 1 provides better MEG/DEG ratio than Example 2 where less conversion was obtained in the plug flow reactor.

Example 3: Comparative Example—Single Plug Flow Reactor

Example 3 was a simulation in which a reactant composition containing water to ethylene oxide ratio of 22:1 was fed to a plug flow reactor where 100% ethylene oxide conversion was achieved. The simulated reaction conditions and results for Example 3 are shown in Table 3.

TABLE 3

| | FEED (100) | PFROUT (102) |
|---|---|---|
| Temperature, ° C. | 145 | 195.29 |
| Pressure, bar | 20 | 20 |
| Flow, Kg/hr | | |
| EO | 43654.95 | 0 |
| Water | 392895 | 375978.73 |
| MEG | 0 | 55168.7 |
| DEG | 0 | 5130.50 |
| TEG | 0 | 272.33 |
| EO conversion in PFR | 100% | |
| Final MEG/DEG ratio (by weight) | 10.75 | |

The MEG ratio can be enhanced by the novel process depicted in both Example 1 and Example 2.

Example 4: Single Plug Flow Reactor+Reactive Distillation Column, Water to Ethylene Oxide Ratio: 12:1 (by Molar) in a Feed Stream to the Plug Flow Reactor Example 4 was simulated for a reactant composition of 12:1 water to ethylene oxide ratio by molar in a plug flow reactor. After an optimum conversion, the reaction mixture was fed to a reactive distillation column where complete reaction was achieved. The simulated reaction conditions and results for Example 4 are shown in Table 4. Comparison between Table 4 and Table 3 shows that

TABLE 4

| | FEED (100) | PFROUT (102) | WATER (104) | FINAL (106) |
|---|---|---|---|---|
| Temperature, ° C. | 145 | 196.71 | 130 | 204.37 |
| Pressure, bar | 20 | 20 | 20 | 15.7 |
| Flow, Kg/hr | | | | |
| EO | 43654.95 | 15915.79 | | 0 |
| Water | 215140 | 204480.60 | 0 | 198394.36 |
| MEG | 0 | 34462.41 | | 54025.80 |
| DEG | 0 | 3705.86 | | 5992.60 |
| TEG | 0 | 230.29 | | 380.36 |
| EO conversion in PFR | | 63.54% | | |
| Final MEG/DEG ratio (by weight) | | 9.02 | | |

In Example 5, the simulation involved a reactant composition containing water to ethylene oxide ratio of 12:1 was fed to a plug flow reactor where 100% conversion was achieved. The simulated reaction conditions and results for Example 5 are shown in Table 5.

TABLE 5

| | FEED (100) | PFROUT (102) |
|---|---|---|
| Temperature, ° C. | 145 | 230.17 |
| Pressure, bar | 20 | 20 |
| Flow, Kg/hr | | |
| EO | 43654.95 | 0 |
| Water | 215140 | 198898.91 |
| MEG | 0 | 50737.64 |
| DEG | 0 | 8351.68 |
| TEG | 0 | 806.72 |
| EO conversion in PFR | 100% | |
| Final MEG/DEG ratio (by weight) | 6.08 | |

Comparison between Table 4 and Table 5 shows that the MEG ratio can be enhanced by the novel process simulated in Example 4 by incorporating plug flow reactor and reactive distillation column concept.

Example 6: Single Plug Flow Reactor+Reactive Distillation Column, Water to Ethylene Oxide Ratio: 25:1 (by Molar) in s Feed Stream to the Plug Flow Reactor Example 6 was simulated for a reactant composition of 25:1 water to ethylene oxide ratio by molar in a plug flow reactor. After an optimum conversion, the reaction mixture was fed to a reactive distillation column where complete reaction was achieved. The simulated reaction conditions and results for Example 6 are shown in Table 6.

TABLE 6

| | FEED (100) | PFROUT (102) | WATER (104) | FINAL (106) |
|---|---|---|---|---|
| Temperature, ° C. | 120 | 158.47 | 130 | 202.40 |
| Pressure, bar | 20 | 20 | 20 | 15.7 |
| Flow, Kg/hr | | | | |
| EO | 43654.95 | 7180.10 | | 0 |
| Water | 446310.35 | 431980.95 | 0 | 429181.9 |
| MEG | 0 | 47400.79 | | 56574.16 |
| DEG | 0 | 3275.14 | | 4043.07 |
| TEG | 0 | 128.31 | | 164.35 |
| EO conversion in PFR | | 83.55% | | |
| Final MEG/DEG ratio (by weight) | | 13.99 | | |

Example 7: Comparative Example—Single Plug Flow Reactor

In Example 7, the simulation involved a reactant composition containing water to ethylene oxide ratio of 25:1 was fed to a plug flow reactor where 100% conversion was achieved. The simulated reaction conditions and results for Example 7 are shown in Table 7. Comparison between Table 6 and Table 7 shows that the system as shown in FIG. 1 is capable of increasing MEG to DEG ratio in the product stream compared to conventional system with a single plug flow reactor when molar ratio of water to ethylene oxide in the feed stream is kept at 25:1.

TABLE 7

| | FEED (100) | PFROUT (102) |
|---|---|---|
| Temperature, ° C. | 120 | |
| Pressure, bar | 20 | 20 |
| Flow, Kg/hr | | |
| EO | 43654.95 | |
| Water | 446310.35 | |
| MEG | 0 | 55862.87 |
| DEG | 0 | 4596.19 |
| TEG | 0 | 215.08 |
| EO conversion in PFR | 100% | |
| Final MEG/DEG ratio (by weight) | 12.16 | |

Example 8: Single Plug Flow Reactor+Reactive Distillation Column, Water to Ethylene Oxide Ratio: 10:1 (by Molar) in a Feed Stream to the Plug Flow Reactor Example 8 was simulated for a reactant composition of 10:1 water to ethylene oxide ratio by molar in a plug flow reactor. After an optimum conversion, the reaction mixture was fed to a reactive distillation column where complete reaction was achieved. The simulated reaction conditions and results for Example 8 are shown in Table 8

TABLE 8

| | FEED (100) | PFROUT (102) | WATER (104) | FINAL (106) |
|---|---|---|---|---|
| Temperature, ° C. | 160 | 218.95 | 130 | 205.17 |
| Pressure, bar | 20 | 20 | 20 | 15.7 |
| Flow, Kg/hr | | | | |
| EO | 43654.9 | 17525.97 | | 0 |
| Water | 178524.13 | 168560.7 | 0 | 161872.42 |
| MEG | 0 | 31951.87 | | 53405.92 |
| DEG | 0 | 3869.58 | | 6452.54 |
| TEG | 0 | 270.91 | | 446.35 |
| EO conversion in PFR | | 59.85% | | |
| Final MEG/DEG ratio (by weight) | | 8.28 | | |

Example 9: Comparative Example—Plug Flow Reactor

In Example 9, the simulation involved a reactant composition containing water to ethylene oxide ratio of 10:1 was fed to a plug flow reactor where 100% conversion was achieved. The simulated reaction conditions and results for Example 9 are shown in Table 9. Comparison between Table 8 and Table 9 shows that the system as shown in FIG. 1 is capable of increasing MEG to DEG ratio in the product stream compared to conventional system with a single plug flow reactor when molar ratio of water to ethylene oxide in the feed stream is kept at 10:1.

TABLE 9

| | FEED (100) | PFROUT (102) |
|---|---|---|
| Temperature, ° C. | 160 | |
| Pressure, bar | 20 | 20 |
| Flow, Kg/hr | | |
| EO | 43654.95 | 0 |
| Water | 178524.14 | 162562.95 |
| MEG | | 48934.66 |
| DEG | | 9570.85 |
| TEG | | 1110.46 |
| EO conversion in PFR | 100% | |
| Final MEG/DEG ratio (by weight) | 5.11 | |

Case B: Simulation of an Ethylene Glycol Production System Comprising a First Reactor, a Separation Unit, and a Second Reactor in Series as Shown in FIG. 2

Simulations of ethylene glycol production using the system as shown in FIG. 2 were run in Aspen™ Plus platform. A reaction temperature of 145° C. is used in first reactor. The simulated reaction conditions and results are shown in Table 10.

Example 10: Ethylene Glycol Production in a System Comprising Two Plug Flow Reactors and a Separation Unit in Series at a Reaction Temperature of 145° C.

TABLE 10

| Stream number | | 200 | 202 | 204 | 205 | 207 |
|---|---|---|---|---|---|---|
| Temperature | ° C. | 145 | 170.00996 | 129.3 | 212.9718 | 214.5161 |
| Pressure | bar | 20 | 20 | 20 | 20 | 20 |
| Mass Flows | kg/hr | 436549.95 | 436549.95 | 42414 | 394135.6 | 394135.9 |
| WATER | kg/hr | 392895 | 384286.32 | 21655 | 362630.9 | 362141.6 |
| MEG | kg/hr | 0 | 28847.83 | 14.17 | 28836.71 | 30422.64 |
| DEG | kg/hr | 00 | 1362.1903 | 0.047 | 1362.266 | 1528.2 |
| TEG | kg/hr | | 36.557533 | 0.001 | 36.56072 | 43.44321 |
| PEG | kg/hr | 0 | 0 | 0 | 0 | 0 |
| EO | kg/hr | 43654.95 | 22017.048 | 20746 | 1269.195 | 0 |

Although embodiments of the present invention have been described with reference to blocks of FIGS. 3 and 4, it should be appreciated that operation of the present invention is not limited to the particular blocks and/or the particular order of the blocks illustrated in FIGS. 3 and 4. Accordingly, embodiments of the invention may provide functionality as described herein using various blocks in a sequence different than that of FIGS. 3 and 4.

In the context of the present invention, at least 37 embodiments are now described. Embodiment 1 is a method of producing alkylene glycol. The method includes the steps of flowing a feed stream comprising alkylene oxide and water into a first reactor unit; subjecting the alkylene oxide and water, in the first reactor unit, to first reaction conditions such that an effluent of the first reactor unit comprises an alkylene glycol, unreacted alkylene oxide, and unreacted water; flowing at least a portion of the unreacted alkylene oxide and unreacted water to a second reactor unit; and subjecting the unreacted alkylene oxide and unreacted water in the second reactor unit to second reaction conditions sufficient to produce additional alkylene glycol; wherein the second reactor unit is a reactive distillation column and higher mono alkylene to di alkylene glycol ratio is produced even at lower water to alkylene oxide ratio. Embodiment 2 is the method of embodiment 1, wherein the alkylene glycol is ethylene glycol and the alkylene oxide is ethylene oxide. Embodiment 3 is the method of any of embodiments 1 and 2, wherein the first reactor unit includes a plug flow reactor adapted to provide the first reaction conditions therein. Embodiment 4 is the method of embodiment 3, further including the step of flowing a stream of water to the reactive distillation column. Embodiment 5 is the method of embodiment 4, wherein the water enters the reactive distillation column at a temperature in a range of 125° C. to 150° C. Embodiment 6 is the method of any of embodiments 3 to 5, wherein the reactive distillation column is further adapted for reaction and distilling liquids and the method further includes reaction and distillation in the reactive distillation column, the effluent of the first reactor unit to produce (1) an overhead stream comprising unreacted water and unreacted ethylene oxide and (2) a bottoms stream comprising unreacted water and mono ethylene glycol; and recycling at least a portion of the overhead stream back to the reactive distillation column as reflux. Embodiment 7 is the method of embodiment 6, wherein the bottoms stream further comprises diethylene glycol, and/or triethylene glycol. Embodiment 8 is the method of any of embodiments 1 to 2, further including the steps of reaction and separation, in the reactive distillation column, the effluent of the first reactor unit into a first stream containing primarily unreacted water and unreacted ethylene oxide, collectively, and a second stream containing primarily unreacted water, and mono ethylene glycol, unreacted ethylene oxide, collectively; flowing the second stream into the second reactor unit; and subjecting the second stream, in the second reactor unit, to the second reaction conditions. Embodiment 9 is the method of embodiment 8, wherein the second stream further includes diethylene glycol and/or triethylene glycol. Embodiment 10 is the method of any of embodiments 8 and 9, wherein the second reaction conditions in the second reactor unit are non-catalytic reaction conditions. Embodiment 11 is the method of any of embodiments 8 to 10, wherein the second reaction conditions in the second reactor unit include a reactor inlet temperature in a range of 160 to 220° C. and a reaction pressure of 10 to 20 bar. Embodiment 12 is the method of any of embodiments 8 to 11, further including recovering at least a portion of ethylene oxide from the first stream for pure ethylene oxide production. Embodiment 13 is the method of any of embodiments 1 to 12, wherein the first reactor has a reaction residence time of 0.5 to 8 minutes. Embodiment 14 is the method of claim 13, further comprising recovering at least a portion of ethylene oxide from the first stream for pure ethylene oxide production. Embodiment 15 is the method of any of embodiments 2 to 14, wherein the effluent of the first reactor unit further includes diethylene glycol and/or triethylene glycol. Embodiment 16 is the method of any of embodiments 2 to 15, wherein the first reaction conditions and second reaction conditions are non-catalytic reaction conditions. Embodiment 17 is the method of any of embodiments 2 to 16, wherein the reaction conditions in the first reactor unit include a reactor inlet temperature in a range of 120 to 160° C., a reaction pressure of 18 to 25 bar, and a residence time of 0.5 to 8.0 minutes.

Embodiment 18 is method of producing ethylene glycol. The method includes the steps of flowing ethylene oxide and water into a first reactor, subjecting the ethylene oxide and water in the first reactor to reaction conditions sufficient to produce ethylene glycol such that a first effluent stream of the first reactor contains mono ethylene glycol, unreacted ethylene oxide, and unreacted water; separating, in a separation unit, the first effluent stream into a first stream containing primarily unreacted water and unreacted ethylene oxide, collectively and a second stream containing primarily unreacted ethylene oxide, unreacted water, and mono ethylene glycol, collectively; flowing the second stream into a second reactor; and subjecting the second stream in the second reactor to reaction conditions sufficient to produce additional mono ethylene glycol; wherein the second reactor unit is a reactive distillation unit. Embodiment 19 is the method of embodiment 18, further including the step of recycling at least a portion of the first stream to the first reactor for producing additional ethylene glycol. Embodiment 20 is the method of any of embodiments 8 or 18, wherein the separating of first effluent stream to produce first stream and second stream is performed at an overhead boiling temperature range of 150 to 180° C. and a pressure range of 6 to 20 bar. Embodiment 21 is the method of any of embodiments 18 to 20, wherein the effluent of the first reactor further contains diethylene glycol and/or triethylene glycol. Embodiment 22 is the method of either of embodiments 18 to 21, wherein the second stream further contains diethylene glycol and/or triethylene glycol. Embodiment 23 is the method of any of embodiments 18 to 22, wherein the reaction conditions in the first reactor are non-catalytic reaction conditions. Embodiment 24 is the method of any of embodiments 18 to 23, wherein the reaction conditions in the second reactor are non-catalytic reaction conditions. Embodiment 25 is the method of any of embodiments 18 to 24, wherein all the ethylene oxide flowed into the second reactor are converted in the second reactor. Embodiment 26 is the method of any of embodiments 18 to 25, wherein the reaction conditions in the first reactor include a reaction temperature in a range of 130 to 150° C. Embodiment 27 is the method of any of embodiments 18 to 26, wherein the reaction conditions in the first reactor include a reaction pressure of 18 to 22 bar. Embodiment 28 is the method of any of embodiments 18 to 27, wherein the reaction conditions in the first reactor include a residence time of 0.5 to 1.0 minute. Embodiment 29 is the method of any of embodiments 18 to 28, wherein the reaction conditions in the second reactor include a reaction temperature in a range of 160 to 180° C. Embodiment 30 is the method of any of embodiments 18 to 29, wherein the reaction conditions in the second reactor include a reaction pressure of 10 to 20 bar. Embodiment 31 is the method of any of embodiments 18 to 30, wherein the reaction conditions in the first reactor comprise a residence time of 5 to 8 minutes. Embodiment 32 is the method of any of embodiments 18 to 31, wherein the effluent of the first reactor is separated in a distillation column. Embodiment 33 is the method of any of embodiments 18 to 32, wherein the method is capable of producing mono ethylene glycol and diethylene glycol at a molar ratio of 15 to 18.5. Embodiment 34 is the method of any of embodiments 18 and 19, wherein the method further includes recovering at least a portion of the first stream to an ethylene oxide purification unit for producing ethylene oxide.

Embodiment 35 is a method of producing alkylene glycol. The method includes flowing alkylene oxide and water into a first reactor unit. The method further includes subjecting the alkylene oxide and water, in the first reactor unit, to first reaction conditions such that an effluent of the first reactor unit contains an alkylene glycol, unreacted alkylene oxide, and unreacted water. The method still further includes flowing at least a portion of the unreacted alkylene oxide to a reactive distillation unit. The method also includes subjecting the unreacted alkylene oxide in the reactive distillation unit to second reaction conditions sufficient to produce additional alkylene glycol. Embodiment 36 is a method of producing ethylene glycol. The method includes flowing ethylene oxide and water into a first reactor. The method further includes subjecting the ethylene oxide and water in the first reactor to reaction conditions sufficient to produce ethylene glycol such that a first effluent stream of the first reactor comprises mono ethylene glycol, unreacted ethylene oxide, and unreacted water. The method further includes separating, in a separation unit, the first effluent stream into a first stream comprising primarily unreacted water and unreacted ethylene oxide, collectively and a second stream comprising primarily unreacted ethylene oxide, unreacted water, and mono ethylene glycol, collectively. The method further includes flowing the second stream into a reactive distillation unit. The method further includes subjecting the second stream in the reactive distillation unit to reaction conditions sufficient to produce additional mono ethylene glycol. Embodiment 37 is a method of producing ethylene glycol. The method includes flowing ethylene oxide and water into a first reactor. The method further includes subjecting the ethylene oxide and water in the first reactor to reaction conditions sufficient to produce ethylene glycol such that a first effluent stream of the first reactor comprises mono ethylene glycol, unreacted ethylene oxide, and unreacted water. The method further includes separating, in a separation unit, the first effluent stream into a first stream comprising primarily unreacted water and unreacted ethylene oxide, collectively and a second stream comprising primarily unreacted ethylene oxide, unreacted water, and mono ethylene glycol, collectively. The method further includes flowing the second stream into a second reactor. The method further includes subjecting the second stream in the second reactor to reaction conditions sufficient to produce additional mono ethylene glycol.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of producing alkylene glycol, the method comprising:

flowing a feed stream comprising alkylene oxide and water into a first reactor unit;

subjecting the alkylene oxide and water, in the first reactor unit, to first reaction conditions such that an effluent of the first reactor unit comprises an alkylene glycol, unreacted alkylene oxide, and unreacted water;

flowing at least a portion of the unreacted alkylene oxide and unreacted water to a second reactor unit; and subjecting the unreacted alkylene oxide and unreacted water in the second reactor unit to second reaction conditions sufficient to produce additional alkylene glycol;

wherein the second reactor unit is a reactive distillation column and higher mono alkylene to di alkylene glycol ratio is produced even at lower water to alkylene oxide ratio; and wherein one or both of:

(i) the first reactor unit comprises a plug flow reactor adapted to provide the first reaction conditions therein; or (ii) the first reactor has a reaction residence time of 0.5 to 8 minutes.

2. The method of claim 1, wherein the alkylene glycol is ethylene glycol and the alkylene oxide is ethylene oxide.

3. The method of claim 2, wherein the first reactor unit comprises a plug flow reactor adapted to provide the first reaction conditions therein.

4. The method of claim 3, further comprising:

flowing a stream of water to the reactive distillation column.

5. The method of claim 4, wherein the water enters the reactive distillation column at a temperature in a range of 125° C. to 150° C.

6. The method of claim 3, wherein the reactive distillation column is further adapted for reaction and distilling liquids and the method further comprises:

reactive distilling in the reactive distillation column, the effluent of the first reactor unit to produce (1) an overhead stream comprising unreacted water and unreacted ethylene oxide and (2) a bottoms stream comprising unreacted water and mono ethylene glycol; and recycling at least a portion of the overhead stream back to the reactive distillation column as reflux.

7. The method of claim 6, wherein the bottoms stream further comprises diethylene glycol, and/or triethylene glycol.

8. The method of claim 1, wherein the first reactor has a reaction residence time of 0.5 to 8 minutes.

9. The method of claim 8, further comprising recovering at least a portion of ethylene oxide from the effluent of the first reactor unit for pure ethylene oxide production.

10. The method of claim 2, wherein the effluent of the first reactor unit further comprises diethylene glycol and/or triethylene glycol.

11. The method of claim 2, wherein the first reaction conditions and second reaction conditions are non-catalytic reaction conditions.

12. The method of claim 2, wherein the reaction conditions in the first reactor unit comprise: a reactor inlet temperature in a range of 120 to 160° C., a reaction pressure of 18 to 25 bar, and a residence time of 0.5 to 8.0 minutes.

13. A method of producing an alkylene glycol, the method comprising:

flowing a feed stream comprising alkylene oxide and water into a first reactor;

subjecting the feed stream and water in the first reactor to reaction conditions sufficient to produce alkylene glycol such that a first effluent stream of the first reactor comprises alkylene glycol, unreacted alkylene oxide, and unreacted water;

separating, in a separation unit, the first effluent stream to produce a first stream comprising primarily unreacted water and unreacted alkylene oxide, collectively, and a second stream comprising primarily unreacted water, and alkylene mono glycol, unreacted alkylene oxide, collectively;

flowing the second stream into a second reactor unit; and subjecting the second stream, in the second reactor unit, to the second reaction conditions, wherein one or both of:

i) the separating of first effluent stream to produce the first stream and the second stream is performed at an overhead boiling temperature range of 150 to 180° C. and a pressure range of 6 to 20 bar; or ii) the second reaction conditions in the second reactor unit comprise a reactor inlet temperature in a range of 160 to 220° C. and a reaction pressure of 10 to 20 bar.

14. The method of claim 13, wherein the second reaction conditions in the second reactor unit are non-catalytic reaction conditions.

15. The method of claim 13, wherein the alkylene glycol comprises ethylene glycol.

16. The method of claim 15, wherein the second stream further comprises diethylene glycol and/or triethylene glycol.

17. The method of claim 13, further comprising recovering at least a portion of alkylene oxide from the first stream for pure alkylene oxide production.

18. The method of claim 13, further comprising:

recycling at least a portion of the first stream to the first reactor for producing additional alkylene glycol.

19. The method of claim 13, wherein the separating of first effluent stream to produce first stream and second stream is performed at an overhead boiling temperature range of 150 to 180° C. and a pressure range of 6 to 20 bar.

20. A method of producing alkylene glycol, the method comprising:

flowing a feed stream comprising alkylene oxide and water into a first reactor unit;

subjecting the alkylene oxide and water, in the first reactor unit, to first reaction conditions such that an effluent of the first reactor unit comprises an alkylene glycol, unreacted alkylene oxide, and unreacted water;

flowing at least a portion of the unreacted alkylene oxide and unreacted water to a second reactor unit; and subjecting the unreacted alkylene oxide and unreacted water in the second reactor unit to second reaction conditions sufficient to produce additional alkylene glycol;

wherein the second reactor unit is a reactive distillation column and higher mono alkylene to di alkylene glycol ratio is produced even at lower water to alkylene oxide ratio, wherein the alkylene glycol is ethylene glycol and the alkylene oxide is ethylene oxide, and wherein the reaction conditions in the first reactor unit comprise: a reactor inlet temperature in a range of 120 to 160° C., a reaction pressure of 18 to 25 bar, and a residence time of 0.5 to 8.0 minutes.

* * * * *